United States Patent [19]
Wang et al.

[11] Patent Number: 5,991,665
[45] Date of Patent: Nov. 23, 1999

[54] SELF-COOLING TRANSCUTANEOUS ENERGY TRANSFER SYSTEM FOR BATTERY POWERED IMPLANTABLE DEVICE

[75] Inventors: Xintao Wang; John P. Rosborough, both of Houston; Mohammed Z. A. Munshi, Missouri City, all of Tex.; Edward A. Schroeppel, Boswell, Ga.; Timothy J. Cox, Lake Jackson, Tex.

[73] Assignee: Sulzer Intermedics Inc., Angleton, Tex.

[21] Appl. No.: 08/933,479

[22] Filed: Sep. 18, 1997

[51] Int. Cl.$^6$ .............................. A61N 1/378; H02J 7/00
[52] U.S. Cl. .............................. 607/61; 607/33; 320/108
[58] Field of Search .................... 607/61, 65, 30, 607/32, 33; 320/107, 108, 117

[56] References Cited

U.S. PATENT DOCUMENTS

| | | | |
|---|---|---|---|
| 5,411,537 | 5/1995 | Munshi et al. | 607/33 |
| 5,479,909 | 1/1996 | Schroeppel et al. | 607/33 |
| 5,690,693 | 11/1997 | Wang et al. | 607/61 |
| 5,702,431 | 12/1997 | Wang et al. | 607/61 |
| 5,713,939 | 2/1998 | Nedungade et al. | 607/33 |

OTHER PUBLICATIONS

Alvaro A. Martinez et al., Thermal Sensitivity and Thermotolerance in Normal Porcine Tissues, *Cancer Research*, vol. 43, pp. 2072–2075, May 1983.

S.B. Field et al., The Relationship Between Heating Time and Temperature: Its Relevance to Clinical Hyperthermia, *Radiotherapy and Oncology*, pp. 179–186, 1983.

Luis Felipe Fajardo, Pathological Effects of Hyperthermia in Normal Tissues, *Cancer Research*, vol. 44, pp. 4826s–4833s, Oct. 1984.

Laurie–Roizin–Towle et al., A Comparison of the Heat and Radiation Sensitivity of Rodent and Human Derived Cells Cultured in Vitro, *Radiation Oncology*, vol. 12 No. 1, pp. 647–652, Apr. 1986.

Elwood P. Armour et al., Sensitivity of Human Cells to Mild Hyperthermia, *Cancer Research*, pp. 2740–2744, Jun. 1993.

Kenneth R. Diller et al., Accuracy Analysis of the Henriques Model for Predicting Thermal Burn Injury *ASME*, vol. 268, pp. 117–123, 1993.

Mark W. Dewhirst, Mechanisms of Hyperthermic Cytotoxicity and Effects at the Tissue Level, *ASME*, vol. 268, pp. 133–135, 1993.

*Primary Examiner*—Jeffrey R. Jastrzab
*Attorney, Agent, or Firm*—Schwegman, Lundberg Woessner & Kluth, P.A.

[57] ABSTRACT

A self-cooling transcutaneous energy transfer system is provided for transmitting power to an implantable medical device, such as a defibrillator. The system includes a housing that is supported above the human body by a base so as to define a space between the housing and the body. A primary induction coil is disposed within the housing for transferring electromagnetic energy to the implantable medical device. A cooling fan is attached to the housing for providing forced convective heat transfer from the body. Various power and control circuitry are provided. The system can transfer away heat generated by eddy currents induced in the implantable device by the magnetic flux produced by the induction coil.

18 Claims, 10 Drawing Sheets

SELF-COOLING TRANSCUTANEOUS ENERGY TRANSFER SYSTEM FOR BATTERY POWERED IMPLANTABLE DEVICE

BACKGROUND OF THE INVENTION

1. Field of the Invention

This invention relates generally to recharging systems for implantable medical devices, and more particularly to an external recharging system with forced convection cooling for a battery powered implantable medical device.

2. Description of the Related Art

Many types of implantable medical devices rely on an internal battery pack for primary or backup electrical power. Ventricular assist devices, implantable infusion pumps, pacemakers, and defibrillators represent just a few examples of such devices. Early implantable devices used disposable storage cells almost exclusively, although rechargeable storage cells have also been used in some devices for several years.

Early pacemakers were powered by primary zinc-mercuric oxide cells. Although this system was used for about 15 years, high self-discharge and hydrogen gas evolution presented problems. Furthermore, since these early cells operated at a voltage of 1.5 V, several cells had to be connected in series to obtain the required voltage for pacing.

Over the years, designers have considered many alternative means of power generation and power storage, including primary chemical batteries of all sorts, nuclear batteries, and rechargeable batteries. Consideration was also given to separating the cardiac stimulator system into two parts, a power pack located outside the body that transmits pulses of energy to a passive implanted receiver and a lead. Cardiac pacemakers based on rechargeable nickel-cadmium systems (1.2 V per cell) and rechargeable zinc-mercuric oxide systems (1.5 V per cell) were developed. Although commonly incorporated into many cardiac pacemakers, these systems were unpopular among patients and physicians primarily because the frequency of the recharges was too high (weekly), and the nickel-cadmium system suffered from memory effects which reduced the battery capacity exponentially after each recharge. In addition, the specific energy density of both types of rechargeable batteries was poor, the cell voltages were low, there was no clear state-of-charge indication, and hydrogen gas liberated during overcharge was not properly scavenged either through a recombination reaction or hydrogen getters.

Many present day cardiac pacemakers use non-rechargeable batteries based on a lithium-iodine chemistry. These cells are low current drain devices with a very high energy density and thus can provide a substantial amount of electrical power from a relatively compact sized cell. In addition, lithium-iodine cells are generally not plagued by hydrogen gas evolution. Thus, the housing or can used to enclose the particular implantable device may be hermetically sealed.

Other cardiac stimulators, such as an implantable cardioverter/defibrillator, require higher output currents than lithium-iodine batteries can supply. Such devices typically use a different type of lithium battery employing lithium-silver vanadium oxide chemistry that still functions as a primary battery. Depending upon the severity of the patient's arrhythmia, these implantable defibrillator batteries may last from eighteen months to up to seven years.

Various schemes, such as the use of larger cells and/or the exclusion of collateral or otherwise optional circuitry have been used over the years to lengthen the life of non-rechargeable cells and thus temporarily delay the attendant risks, discomforts, and cost of surgical excision. Larger cell sizes generally yield longer cell life, but also increase the size of the can enclosing the implantable device. Reducing the power consumption of the circuitry in the implantable devices may yield a longer life span for the cell, but will also typically require elimination of collateral circuitry and/or other structure in the implantable device that may provide useful, though not necessarily medically critical functions.

Despite the size and reliability advantages associated with nonrechargeable batteries, there remain several disadvantages associated with these devices. A non-rechargeable cell will, by definition, become depleted within a finite period of time following implantation. Replacement of a depleted non-rechargeable cell requires surgical excision of the entire implantable device.

It is anticipated that future implantable defibrillators will incorporate features such as longer waveform storage, dual chamber pacing, extra sensors, digital signal processing, a combination of defibrillation and drug infusion, among others, all of which will consume extra energy that will reduce the longevity of the storage cell even further. A rechargeable battery that stores adequate energy before recharge would be ideal in such circumstances. Present day advanced rechargeable lithium batteries do not suffer from the same problems as nickel-cadmium or zinc-mercuric oxide batteries. Today's lithium rechargeables have higher voltage and current drain capabilities, and higher capacities with no memory effects. Experiment has shown that these newer batteries require recharge only every 6–12 months, which often coincides with a patient's schedule for routine follow-up medical appointments.

Regardless of the particular chemistry utilized for the rechargeable cell, a recharging system is required to recharge the battery. One such system involves transcutaneous energy transmission. Generally, in a transcutaneous energy transmission system, the implantable medical device is provided with a charging circuit to which energy is transferred by electromagnetic induction. An appliance is placed on or over the skin proximate the implanted device. The appliance is provided with a primary coil. An alternating current in the primary coil induces an alternating current in the charging circuit within the implantable device. The induced alternating current is typically rectified and regulated to provide a direct current for charging the rechargeable cell.

As with nearly all magnetic induction systems, transcutaneous energy transmission gives rise to eddy currents in the housing and various metallic components of the implantable device. The alternating magnetic flux generated by the primary coil not only induces a charging current in the charging circuit of the implantable device, but also induces eddy currents in the device can and various metallic components. The magnitude of the induced eddy currents is a function of the frequency and magnitude of the magnetic flux. An undesirable byproduct of the creation of eddy currents in implantable devices is a temperature increase in the components in which the eddy currents are flowing. The magnitude of the temperature increase in the implantable device is a function of the magnitudes of the eddy currents and the resistances of the components carrying the eddy currents, as well as the total energy transferred during the recharging operation.

Most implantable devices are surrounded by adipose, vascular, and muscular tissues. While it is desirable for heat built up in the implantable device to conduct away through these tissues, implantable device temperatures exceeding certain limits may injure or permanently damage those tissues. The ability of human tissue to withstand hyperthermic conditions is governed by a complex set of factors including the type of tissue involved, the temperature, and the duration of exposure. Although there is no clear cut clinical consensus on the maximum temperature that human tissue can withstand on either an acute or chronic basis without damage, there appears to be a correlation between tissue damage and temperatures above 42° C.

The thermal management of early pacemaker designs seldom required specialized design or unusual charging techniques. Those early designs incorporated relatively small storage cells that required low power levels necessary for recharging. Therefore, those conventional pacemaker designs required more frequent charging, (perhaps weekly), and thus only a relatively small amount of total energy transferred for each charging session. More modern, and high energy consumption systems, such as defibrillators, require a higher transfer of total energy for a given charging. This is due to the higher energy storage requirements of defibrillators as well as the design goal of producing storage cells that require less frequent recharging. Some designs may require recharging every six months. However, each charging session may last two hours or more.

Thermal management for the more powerful rechargeable lithium cell systems has become a matter of concern for designers of new implantable medical devices. Various schemes for heat abatement have been tried with mixed results. Cold packs topically applied to the bare skin transfer heat away by conduction. However, patient comfort is compromised since the icy cold packs must be left on the skin for up to two hours. Two other proposed solutions involve attempts to limit the amount of heat generated rather than transferring the heat that is generated. In one, circuitry is incorporated into the implantable device to manage the charging protocol of the storage cell. The circuitry is complex, consumes space within the device's housing and adds cost to the device. The other proposed solution involves fabricating the device can out of a material that is less conductive and prone to eddy current propagation. However, the available class of biocompatible metallic materials is narrow. No one of those materials exhibits a significantly lower conductivity than the others.

The present invention is directed to overcoming or reducing one or more of the foregoing disadvantages.

SUMMARY OF THE INVENTION

In accordance with one aspect of the present invention, a transcutaneous energy transfer system for transferring energy to an implantable medical device is provided. The transcutaneous energy transfer system includes a housing that has a lower surface and a base for supporting the housing above a patient's skin and thereby defining a space between the lower surface and the patient's skin. An induction coil is provided that is disposed in the housing for transferring energy to the implantable medical device. An electric fan is provided for moving air through the space.

In accordance with another aspect of the present invention, a transcutaneous energy transfer system is provided. The transcutaneous energy transfer system includes a housing that has a lower surface and a base for supporting the housing above a patient's skin and thereby defining a space between the lower surface and the patient's skin. An induction coil is disposed in the housing for transferring energy to the implantable medical device. A controller is coupled to the induction coil for controlling power supplied to the induction coil. An electric fan is coupled to the housing for moving air through the space. A regulator is supplied for controlling the operation of the electric fan in response to the temperature of the implantable device.

In accordance with still another aspect of the present invention, a recharger for transcutaneously recharging a battery in an implantable medical device is provided. The recharger includes a housing that has an annular chamber, an upper surface, and a lower surface. The housing also includes a passage extending from the upper surface to the lower surface that is substantially concentric with the annular chamber, and a base for supporting the housing above a patient's skin and thereby defining a space between the lower surface and the patient's skin. An induction coil is encased within the annular chamber for transferring energy to the battery. An electric fan is coupled to the housing and is disposed within the passage for moving air through the space. A controller is coupled to the induction coil for controlling power supplied to the induction coil. A regulator is provided for controlling the operation of the electric fan in response to the temperature of the implantable device.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
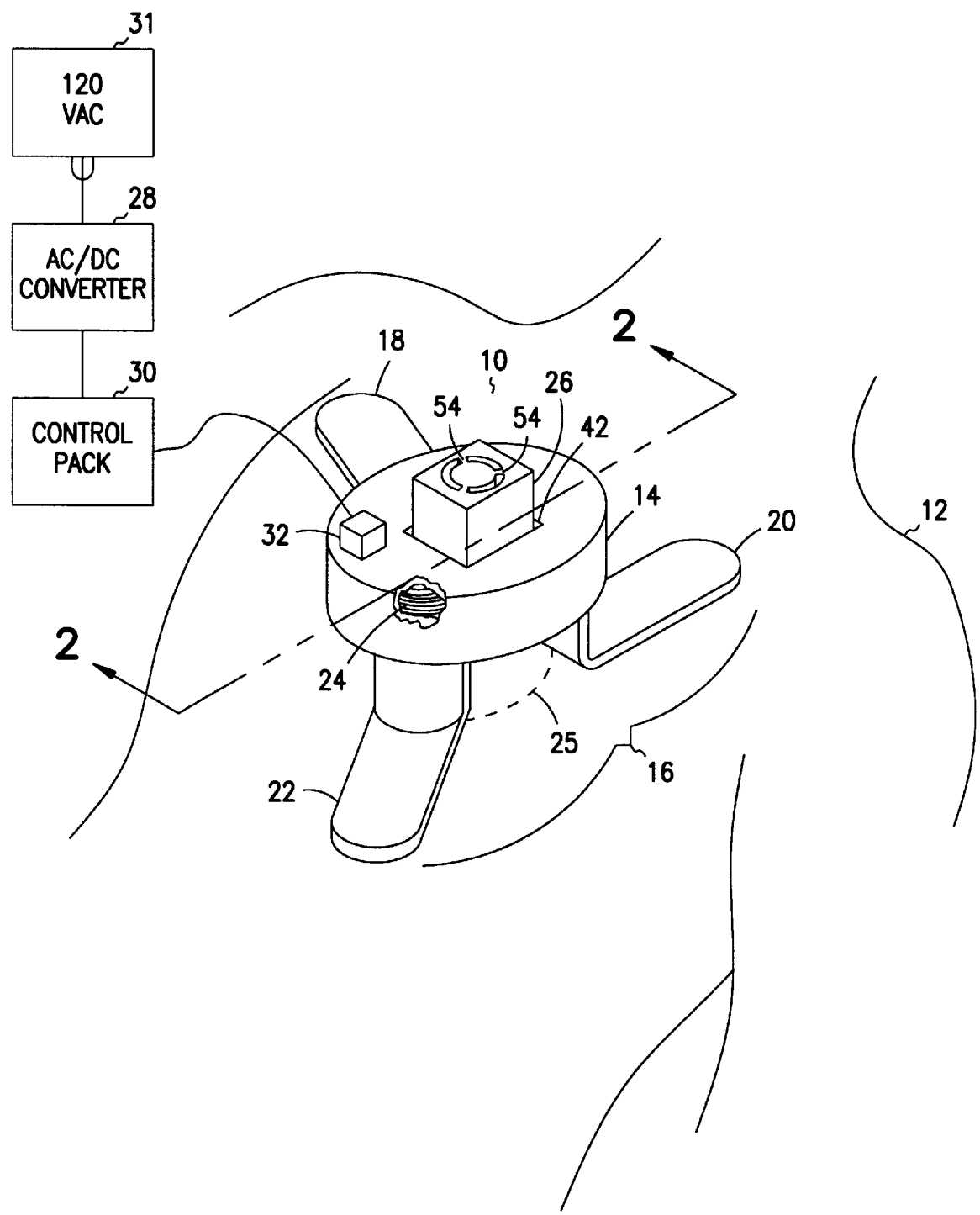
FIG. 1 is a pictorial view of an exemplary embodiment of a self-cooling transcutaneous energy transfer system in accordance with the present invention.

In the drawings described below, reference numerals are generally repeated where identical elements appear in more than one figure. Turning now to the drawings, and in particular to FIG. 1, there is shown an exemplary embodiment of a self-cooling transcutaneous energy transfer system ("TET") 10 disposed on the chest of a human body 12. The TET system 10 includes a housing 14 that is supported above the body 12 by a base 16 consisting of three peripherally spaced legs 18, 20, and 22. A primary induction coil 24 is disposed within the housing 14 for transferring electromagnetic energy to an implantable medical device 25 (shown subcutaneously disposed in phantom). A cooling fan 26 is attached to the housing 14 for providing forced convective heat transfer from the body 12. An AC/DC converter 28 and a control pack 30 are provided to supply power and various control functions to the TET system 10. The AC/DC converter 28 may be coupled to an external power source 31. The box 32 is a schematic representation of the connection between the induction coil 24, the fan 26, and the control pack 30.

Figure 2:
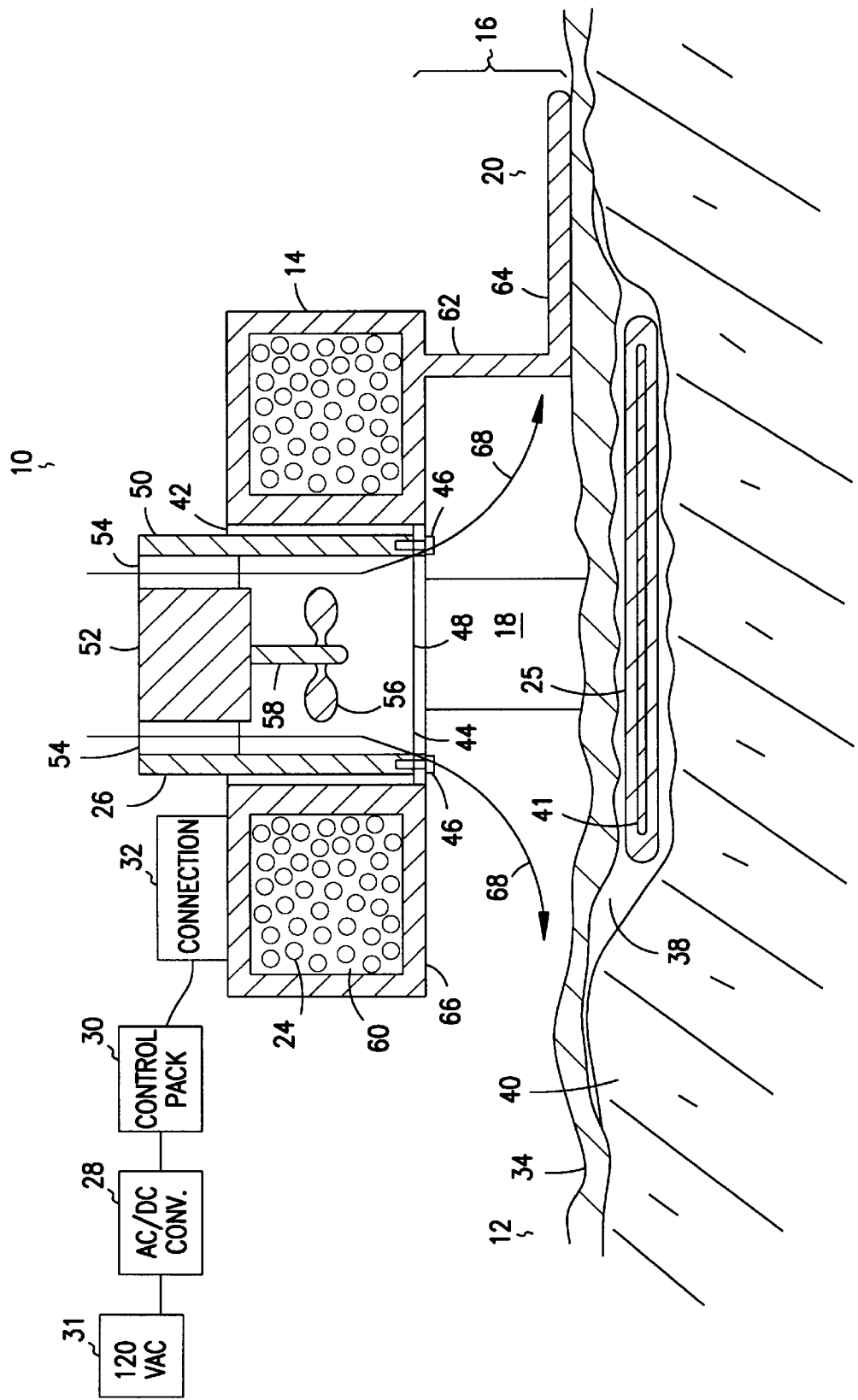
FIG. 2 is a cross-sectional view of FIG. 1 taken at section 2—2.

Referring now also to FIG. 2, which is a cross-sectional view of FIG.1 taken at section 2—2, the TET system is shown resting on the skin 34 of the body 12 and overlying the implantable medical device 25. The skin tissue 34 normally includes several dermal layers and an underlying adipose layer. The implantable device 25 is enclosed within a metallic can 41 that is disposed in a subcutaneous pocket 38 formed between the skin 34 and the underlying muscular tissue 40. The representation of the implantable device 25 is merely schematic in that the particular type, shape, and size of the implantable device 25 and the can 41 are subject to great variation.

The housing 14 has a generally cylindrical shape and is provided with a longitudinally disposed bore 42 that is sized to accommodate the electric fan 26. The lower end of the bore 42 includes a shelf 44 for supporting the electric fan 26 and for providing structure to which the electric fan 26 may be secured to the housing 14 by the bolts 46 as shown. The shelf 44 includes an opening 48 to permit air to flow through the electric fan 26. The housing 14 is provided with an annular chamber 60. The plurality of windings of the induction coil 24 are disposed in the annular chamber 60. The housing 14 is advantageously composed of a light weight electrically insulating material, such as, for example, polycarbonate, ABS, or similar materials.

The induction coil 24 is designed to transcutaneously deliver an alternating magnetic flux to the implantable device 25. The particular type of induction coil 24 selected is a matter of design, although relatively low AC resistance is desirable to reduce heat generation. In the embodiment shown in FIGS. 1 and 2, the induction coil 24 consists of four hundred (400) windings of 38/40 gauge litz wire.

As noted above, the base 16 consists of peripherally spaced legs 18, 20, and 22. Note that the leg 22 is not shown in FIG. 2. Each leg 18, 20, and 22 includes a vertically projecting portion 62 and a radially projecting horizontal portion 64. The horizontal portions 64 enhance the positional stability of the TET system 10 as well as distribute the weight of the TET system 10 over a larger area for better patient comfort. The legs 18, 20, and 22 may be formed integrally with the housing 14 or attached as separate components. The base 16 functions to support the housing 14 above the skin 34, thereby defining a space between the lower surface 66 of the housing 14 and the skin 34. The spacing between the lower surface 66 and the skin 34 prevents heat generated by the fan 26 and the induction coil 24 from conducting to the skin 34, and provides the space through which air may flow for convective heat transfer as discussed more below. The requisite height of the base 16 will largely depend on the magnitude of the eddy currents and the flow rate of the fan 26.

Figure 3:
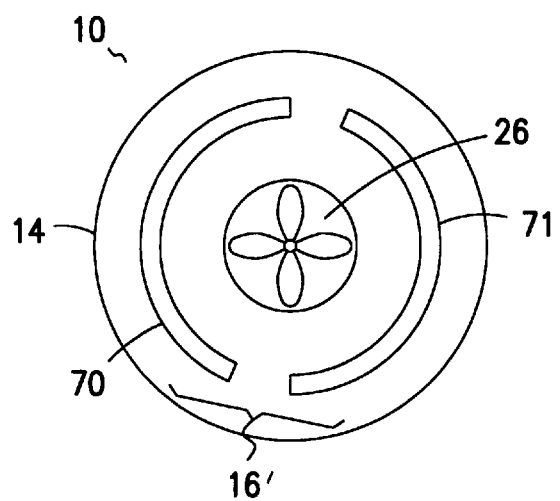
FIG. 3 is a bottom view of an alternate embodiment of the self-cooling transcutaneous energy transfer system of FIG. 1.
Figure 4:
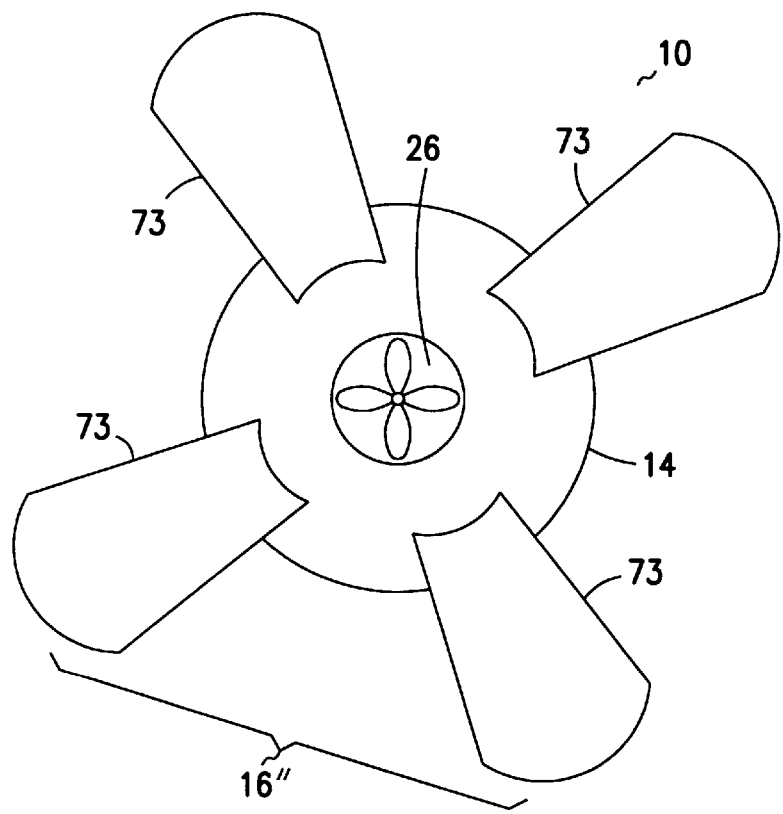
FIG. 4 is a bottom view of an alternate embodiment of the self-cooling transcutaneous energy transfer system of FIG. 1.

The base 16 may take on a variety of other configurations. FIGS. 3 and 4 show bottom views of the TET system 10 incorporating two possible variations for the base, now designated respectively, 16' and 16". As shown in FIG. 3, the base 16' may consist of two peripherally spaced arcuate members 70 and 71. As shown in FIG. 4, the base 16" may consist of four or more peripherally spaced legs 73. The particular number and configuration of the components forming the base 16' or 16" are not critical so long as at least one opening, either between members, such as 70 and 71, or between adjacent legs 73, is provided so that air may readily flow to or from the fan 26 and across the skin 34.

Figure 5:
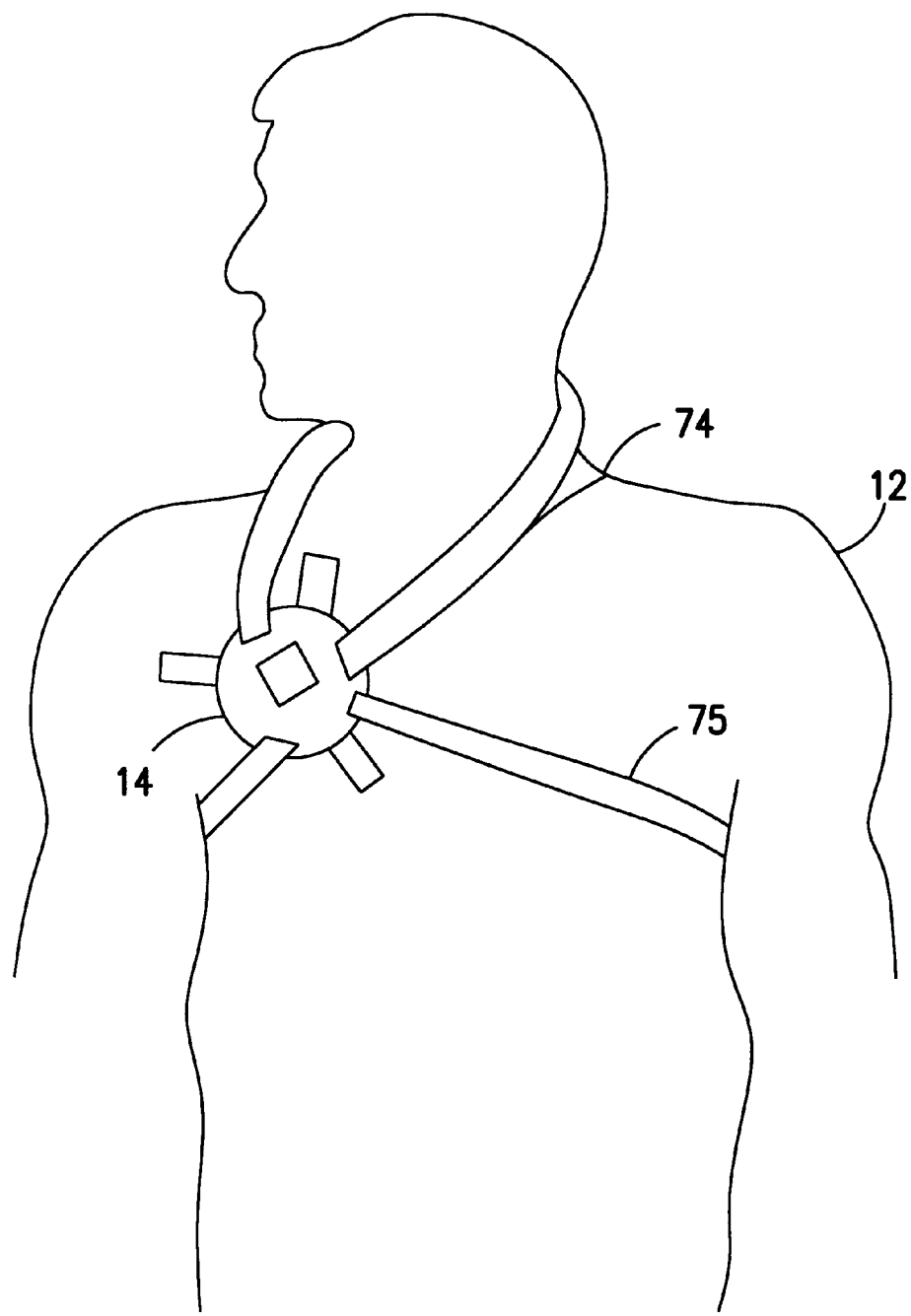
FIG. 5 is a front view of a patient with the self-cooling transcutaneous energy transfer system secured thereto in accordance with the present invention.

The housing 14 may be placed on the patient's body with the patient in a supine position as shown in FIG. 1, and secured as necessary with tape (not shown). However, the removal of tape from a patient's skin may involve some discomfort for the patient. Alternatively, the housing 14 may be fitted with a strap 74 that loops around the patient's neck as shown in FIG. 5. The strap 74 can suspend the housing 14, enabling the patient to wear the housing 14 while in a sitting or semi-reclined position. Additional straps, such as the trunk strap 75 may be fitted to the housing 14 to further secure the housing 14 to the patient.

Referring again to FIGS. 1 and 2, alternating magnetic flux generated by the induction coil 24 produces eddy currents in the can 41, which in turn, cause the temperature of the can 41 to climb. The heat generated in the can 41 is conducted to the surrounding skin and muscle tissues 34 and 40 causing a temperature rise in those tissues 34 and 40. In the absence of a mechanism to transfer the heat conducted by the can 41, the temperature of the skin and muscle tissues 34 and 40 may rise 3.0° C. or more above normal body temperature. In this regard, the fan 26 provides a flow of air in the space to transfer heat away from the skin 34 by forced convection. As the temperature of the skin 34 is lowered by forced convection, a temperature gradient will be established between the skin 34 exposed to airflow and the upper surface of the can 41. Heat generated in most, if not all, of the can 41 will conduct to the skin 34 along this temperature gradient. In this way, the temperature of the entire exterior of the can 41, and thus the surrounding tissues 34 and 40 may be maintained below temperatures associated with tissue injury (e.g. < approximately 42° C.).

The fan 26 includes a cylindrical shell housing 50 and a centrally disposed motor 52 that is coupled at the upper end of the housing 50 by webs 54. Two or more fan blades 56 are connected to a shaft 58 coupled to the motor 52. When the fan 26 is operating, air is moved along the flow path represented by the arrows 68. Air may be thrust downward or pulled upward by selecting the direction of rotation of the fan 26. The particular configuration of the fan 26 is largely a matter of design discretion. Relatively low acoustical noise (<70 dB) is desirable for patient comfort considerations. Some possible types include Elina models HDF3020L-12MB and FDC40-12H 12V DC brushless motor fans made by Inaba Denki Sangyo, Co., Ltd. of Japan.

The discharge of the fan 26 necessary to effectively cool the skin 34 is a function of a variety of factors, such as the power drawn by the implantable device 25 during recharging (a reflection of the magnitude and frequency of the alternating magnetic flux delivered), the type and configuration of the can 41, the size of the gap between the housing 14 and the skin 34, and the condition and thickness of the skin 34. Experiment on a canine subject has shown that, for an implantable device 25 consisting of a defibrillator housed in a titanium can 41 and incorporating a charging circuit drawing 100 mA at 3.6 V, an Elina model HDF3020L-12MB fan 26 delivering 0.022 $m^3$/min at a static pressure of 2.0 mm Hg prevented the temperature of the tissue surrounding the can 41 from climbing after the induction coil 24 was activated, and actually brought the temperature of the tissue down 1.0° C.

Figure 6:
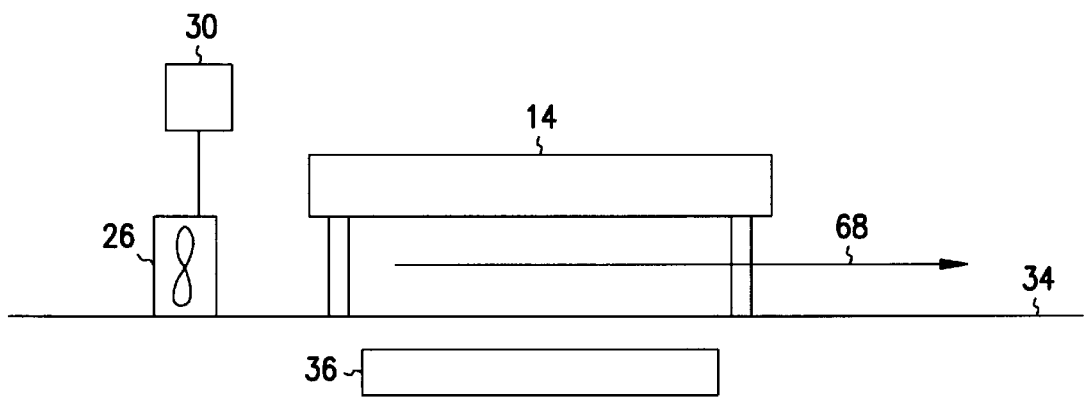
FIG. 6 is a side view of an alternate embodiment of the self-cooling transcutaneous energy transfer system of FIG. 1 in accordance with the present invention.
Figure 7:
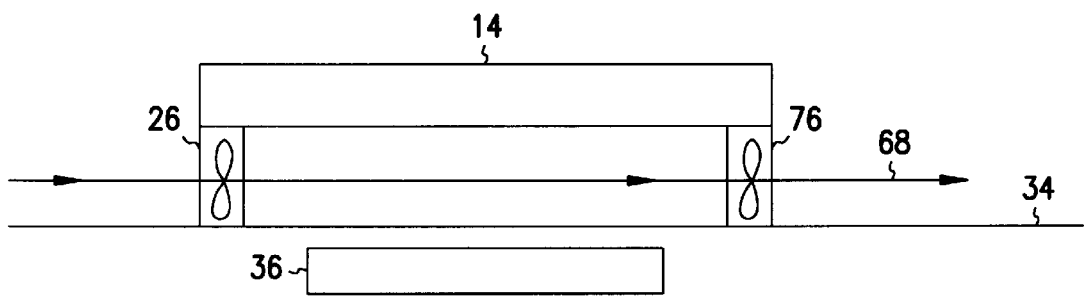
FIG. 7 is a side view of another alternate embodiment of the self-cooling transcutaneous energy transfer system of FIG. 1 in accordance with the present invention.
Figure 8:
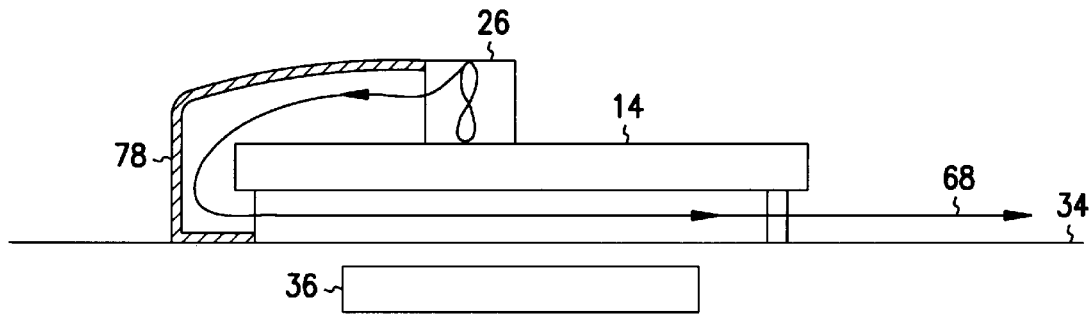
FIG. 8 is a side view of another alternate embodiment of the self-cooling transcutaneous energy transfer system of FIG. 1 in accordance with the present invention.

The manner in which air is forced across the skin 34 may be varied. In this regard, FIGS. 6, 7, and 8 show side views of three possible arrangements of the fan 26 and the housing 14 disposed over the implantable device 25. In FIG. 6, the fan 26 is disposed adjacent, but not physically connected, to the housing 14, and is coupled to the control pack 30. The flow path of air is horizontal along the skin 34 as shown by the arrow 68. In FIG. 7, two fans 26 and 76 are provided. The fans 26 and 76 are disposed in a parallel arrangement between the housing 14 and the skin 34. The flow path is horizontal along the skin 34 as shown by the arrow 68. In FIG. 8, the housing 14 is provided with a duct 78 that leads from the fan 26 mounted on top of the housing 14 to the space between the housing 14 and the skin 34. The flow path is given by the arrow 68. The skilled artisan will appreciate that the direction of airflow represented by the arrow 68 in FIGS. 6, 7, and 8 is exemplary in that the direction of airflow may be left-to-right or vice versa depending upon the direction of rotation of the fan 26 and/or the fan 76.

Figure 9:
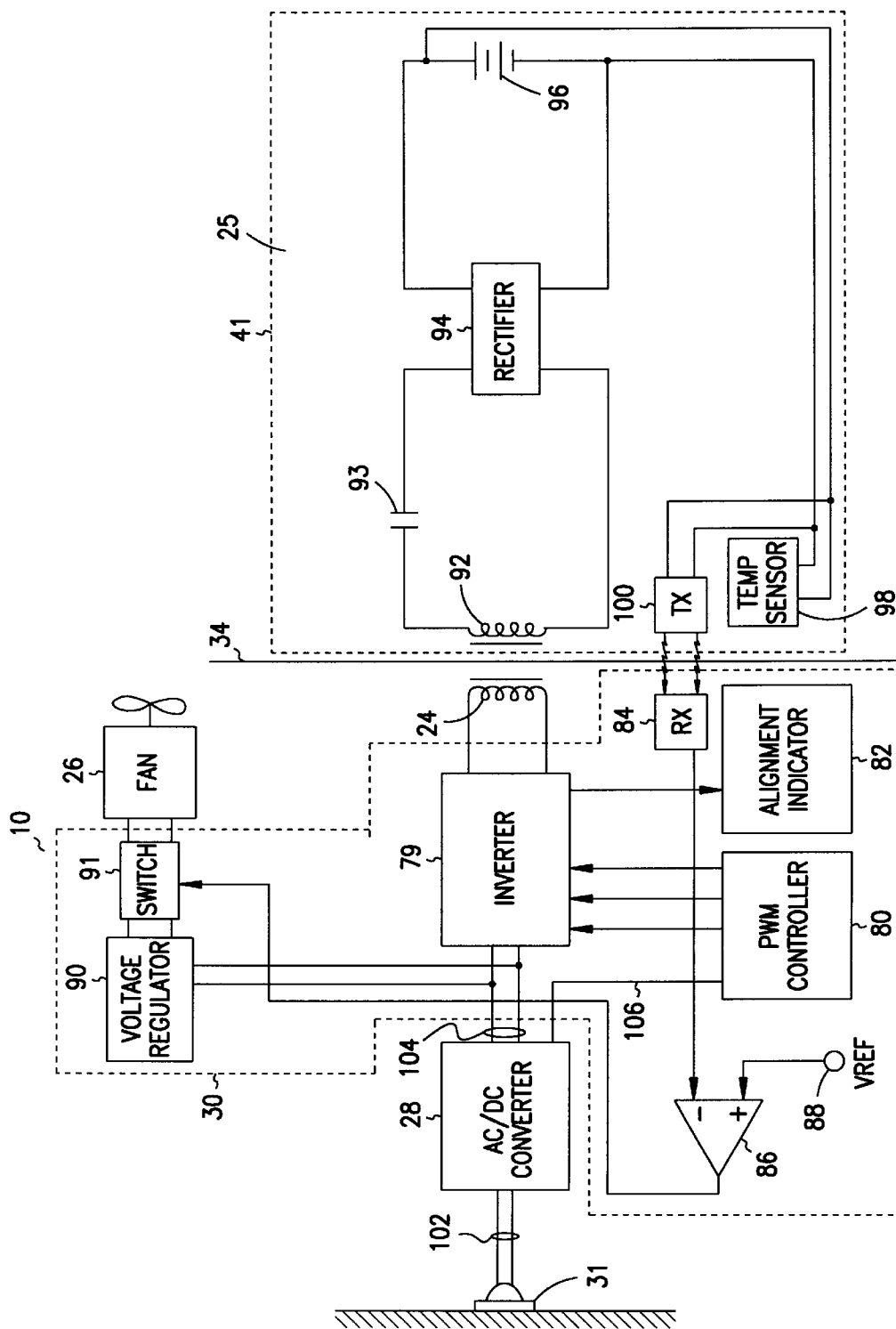
FIG. 9 is a schematic of exemplary circuitry for the self-cooling transcutaneous energy transfer system of FIG. 1 invention in accordance with the present invention.

The electrical circuitry for the TET system 10 may be understood by referring initially to FIG. 9, which is a schematic view of the TET system 10 and the implantable device 25. The control pack 30, generally circumscribed by the dashed box also labeled 30, includes an inverter 79, a controller 80, an alignment indicator 82, a telemetry receiver 84, a comparator 86, a reference voltage source 88, a voltage regulator 90, and a switch 91. The connections to the AC/DC converter 28 and the fan 26 will be described more below.

The implantable device 25 includes a secondary coil 92, a rectifier 94, a battery 96, a temperature sensor 98, and a telemetry transmitter 100. A tuning capacitor 93 is series connected to the secondary coil 92. The rectifier 94 converts the sinusoidal voltage received by the secondary coil 92 to a DC voltage for charging the battery 96. The rechargeable battery 96 may incorporate any of a number of different lithium chemistries, such as those disclosed in commonly assigned U.S. Pat. No. 5,411,537, or any of a variety of other chemistries.

The AC/DC converter 28 is connected to the external power supply 31 by way of the connection cord 102. In this example, the external power source 31 is a 120 volt AC wall outlet. The AC/DC converter 28 converts the 120 volt AC voltage substantially to a DC voltage and regulates that DC voltage at a level that is appropriate for transcutaneous energy transmission. The appropriate voltage level will depend on the type of induction coil 24. In an exemplary embodiment, the DC voltage level may be between 15 and 40 V. Note that the AC/DC converter 28 can be eliminated if the power source 31 is a dedicated DC voltage source.

The inverter 79 receives the regulated DC voltage output signal of the AC/DC converter 28 via conductors 104. The inverter 79 converts the regulated DC voltage output to a sinusoidal current that flows through the induction coil 24. The sinusoidal current flowing through the induction coil 24 produces a time varying magnetic flux which induces a corresponding current in the secondary induction coil 92 in the implantable device 25.

The controller 80 is a pulse width modulation controller that controls the output power level of the inverter 79, and thus, the charging current induced in the secondary induction coil 92. The controller 80 may also periodically interrupt the current supplied to the induction coil 24 to provide a duty-cycled charging current. Power is supplied to the controller 80 from the AC/DC converter 28 via a conductor 106.

The alignment indicator 82 provides a visual indication of when the TET system 10 is properly positioned with respect to the implantable device 25 for maximum charging efficiency. The alignment indicator 82 is connected to one output of the inverter 79.

Figure 10:
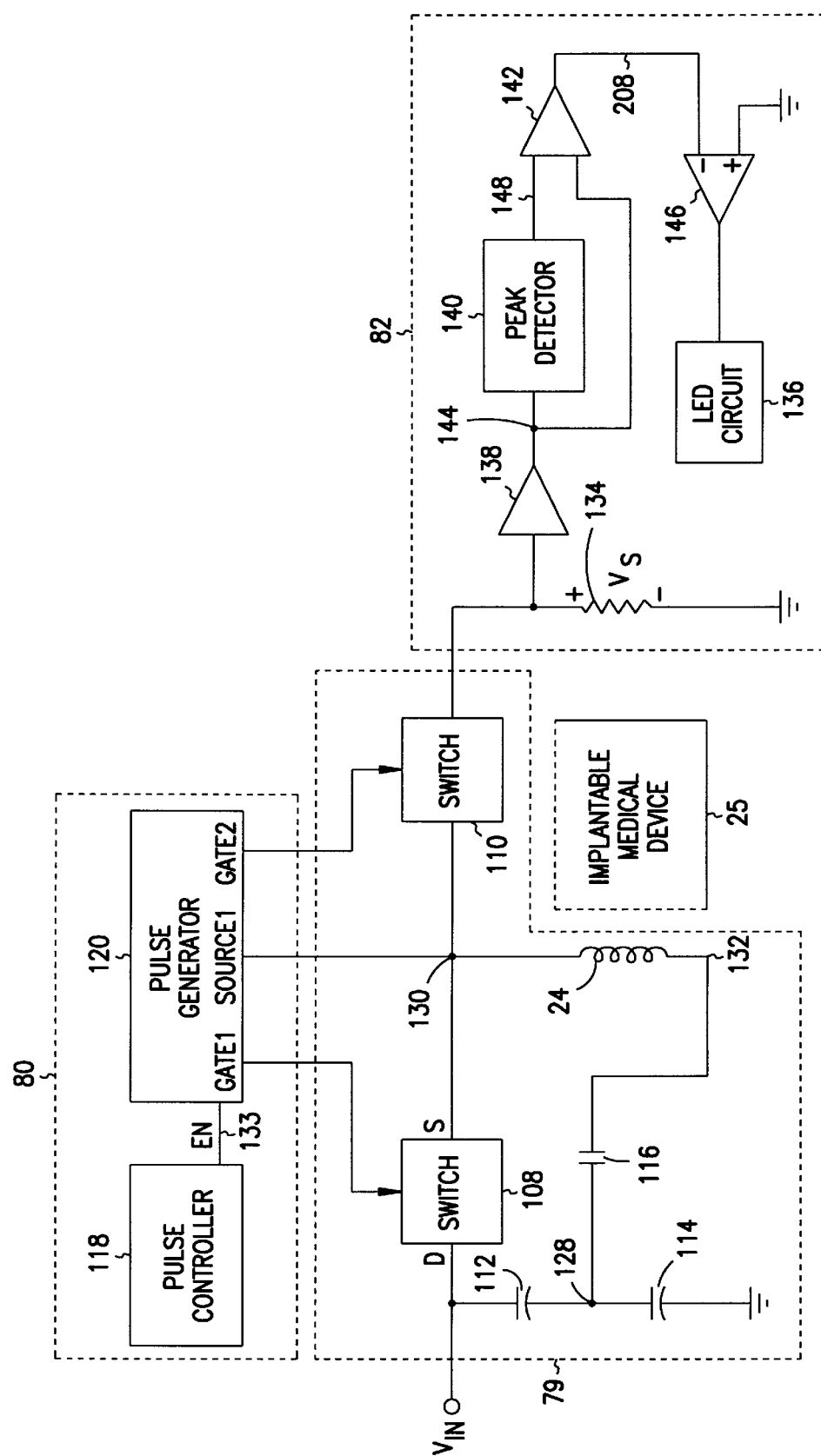
FIG. 10 is a block schematic of the controller, the AC/DC converter, and the alignment indicator shown in FIG. 9 in accordance with the present invention.

More detailed representations of the inverter 79, the controller 80, and the alignment indicator 82 are shown FIGS. 10, 11, 12, 13, and 14. Referring initially to FIG. 10, the inverter 79 includes a pair of switches 108 and 110, a pair of capacitors 112, 114, and a tuning capacitor 116. The PWM controller 80 preferably includes a pulse controller 118 and a pulse generator 120. One of ordinary skill in the art will recognize other circuit implementations are possible for PWM controller 80. The PWM controller 80 advantageously includes functions such as dual output capacities, high source and sink current, and floating ground (SOURCE1 for 108).

Eddy current generation can be reduced by generating a charging current signal that has a substantially full sinusoidal waveform with little harmonic content. To generate the desired symmetrical sinusoidal waveform, the inverter 79 is provided with switches 108 and 110. These switches 108, 110 are advantageously implemented as solid state devices and, as shown in FIG. 10, may be implemented with metal oxide field effect transistors (MOSFET's) 108 and 110. The output of the pulse generator 120 turns the switches 108 and 110 on and off alternately such that only one switch is "on" (i.e., conducting electricity) at any given time. A short time period (for example, 2 microseconds) is provided after one switch turns off and before the other switch turns on. This "dead time" between activation of switches 108, 110 insures that the switches are not on simultaneously which may cause a short circuit condition between the voltage input terminal $V_{in}$ and ground. Increasing the time when both switches 108 and 110 are off results in a decrease in the power supplied to the induction coil 24.

The switches 108 and 110 preferably are turned on for the same amount of time each cycle to produce a symmetrical voltage waveform across the junctions 128 and 130. The capacitors 112 and 114, which advantageously have identical values, form a voltage divider network. The tuning capacitor 116 connects between the common connection point for capacitors 112 and 114 (junction 128) and the terminal 132 of the coil 24.

In order to minimize the eddy current induced in the can 41 of implantable device 25, the operational (or carrier)

frequency of the PWM controller 80 preferably is set at 5 KHz, but it may be set to operate within a range of 1 KHz and 40 KHz. The tuning capacitor 116 is selected to generate the desired current amplitude with the induction coil 24 leakage inductance so that a sinusoidal alternating current waveform flows through the induction coil 24 with little high frequency harmonics. Through proper selection of the value of capacitor 116, the natural resonant frequency of the resonant circuit formed by induction coil 24 and the capacitor 116 can be controlled to be slightly less than the operational frequency in order to achieve the zero-voltage turn-on of both switches 108 and 110.

In general, the inverter 79 produces a purely sinusoidal transfer current waveform between the coils 24 and 92 using a resonant circuit comprising the leakage inductance of induction coil 24 and the tuning capacitor 116. Resonance is continuously maintained by alternately activating switches 108 and 110. The present invention can provide a wide range of charging current from 0 to 1 amperes and charging voltage from 0 to 20 V. The distance between the coil 24 and the coil 92 advantageously is less than 2.5 inches. Although a purely sinusoidal current waveform is advantageous to reduce eddy currents (and thus temperature elevation) which in part are created by higher frequency harmonics, the present invention separately controls temperature rises by using the aforementioned forced convection.

The pulse generator 120 preferably includes an enable input terminal (EN) which controls the status of the controller 80. When an enable signal is provided to the enable input via line 133, the controller 80 is enabled. Conversely, if a disable signal appears on the line 133, the controller 80 is disabled. More specifically, the pulse generator 120 is enabled and disabled. The enable/disable signal on line 133 is used to define a duty cycle for the current delivered to the induction coil 24.

Referring still to FIG. 10, the alignment indicator 82 provides a visual indication of when the TET system 10 is properly positioned with respect to the implantable device 25 for maximum charging efficiency. When the switch 110 is turned on by the controller 80, current flows from the induction coil 24 through the switch 110 and to the resistor 134 in the alignment indicator 82. Due to the symmetric AC current on the induction coil 24, the current through the switch 110 comprises half of the coil current during one-half the time of each cycle of the AC waveform. Thus, only half of the primary coil current is received by resistor 134. In an exemplary embodiment, the DC component of the voltage across the resistor 134 is used as an indication of DC input current from the voltage source $V_{in}$.

The alignment indicator 82 includes a light emitting diode (LED) in LED circuit 136 or other output device to indicate proper positioning of the TET system 10 with respect to implantable device 25. The TET system 10 can be tuned so that the amplitude of the AC current through the induction coil 24 decreases when the coil 24 is not properly aligned with the secondary coil 92. The input DC current, therefore, depends on the power draw of the load on the secondary coil 92 and the proximity and orientation of the induction coil 24 to the secondary coil 92. Therefore, a measurement of the magnitude of the input current preferably is used in the present invention to determine if the TET system 10 is positioned properly for maximum energy transmission efficiency. The following discussion details the construction and operation of the alignment indicator 82 which uses the correlation between the input current and alignment to provide an output signal which indicates when the TET system 10 is sufficiently aligned with the secondary coil 92.

The resistance value of resistor 134 preferably is small to minimize the loading effect on the inverter 79 that would otherwise result. In an exemplary embodiment, resistor 134 is selected as approximately 0.5 ohms. It should be understood that the purpose of resistor 134 is to sense current in the induction coil 24 and provide an output signal indicative of the current amplitude and phase shift. Accordingly, although a resistor is depicted, any current sensing device can be used in place of the resistor 134.

Referring still to FIG. 10, the alignment indicator 82 includes a low-pass amplifier 138, a peak detector 140 to detect the peak DC current amplitude through the switch 110, a differential amplifier 142 to amplify the difference between the peak current amplitude and the amplitude of the output current signal from the low-pass amplifier 138 on the line 144, a comparator 146 to compare the amplified difference with ground voltage, and the LED or other output circuit 136. In the illustrated embodiment, the LED circuit 136 (or other output device) only provides an output signal indicating alignment if the present sensed current amplitude is within a predetermined range of the peak value.

Current flow through the resistor 134 from the switch 110 generates a voltage $V_s$ across the resistor 134 which is amplified and filtered by the low-pass amplifier 138 to effectively obtain the DC component of the waveform through the resistor 134, and to filter out the AC portion of the waveform. The peak detector 140 senses the peak amplitude value of the output signal on the line conductor 144, which connects to the output terminal of the low-pass amplifier 140. The peak detector 140 stores the peak value, unless a higher amplitude is subsequently sensed. If a higher value is subsequently sensed, the peak detector 140 replaces the stored peak value with the new peak value. The output signal of the peak detector 140 on the conductor 148 corresponds to the peak positive voltage sensed by the peak detector 140. This peak voltage (which is scaled to provide a threshold value that is somewhat less than the peak value), is provided as an input to the differential amplifier 142. The other input to the differential amplifier comprises the current sensed output of the low-pass amplifier 138 (conductor 144). The differential amplifier 142 amplifies the difference between the scaled peak value, and the present sensed value, and provides an output signal to comparator 146.

The comparator 146 compares the difference with ground voltage, and turns on the LED circuit 136 when the current sensed value is greater than the scaled peak value. This condition will occur when the TET system 10 is positioned properly over the implantable device 25. In order to capture the optimum location, the induction coil 24 has to pass the optimal location at least once to let the peak detector 140 record the peak DC current value. Thereafter, the LED circuit 136 will not be turned on unless the induction coil 24 stays at the optimum location and orientation. If the lateral placement of the TET system is misaligned with respect to the secondary coil 92, or if the TET system 10 is positioned at a nonoptimal angle with respect to the implanted device for peak transmission efficiency, the scaled peak value will be greater than the present output voltage at the output terminals of the filter 138, and the comparator 146 will produce an output signal de-activating the LED circuit 136.

Figure 11:
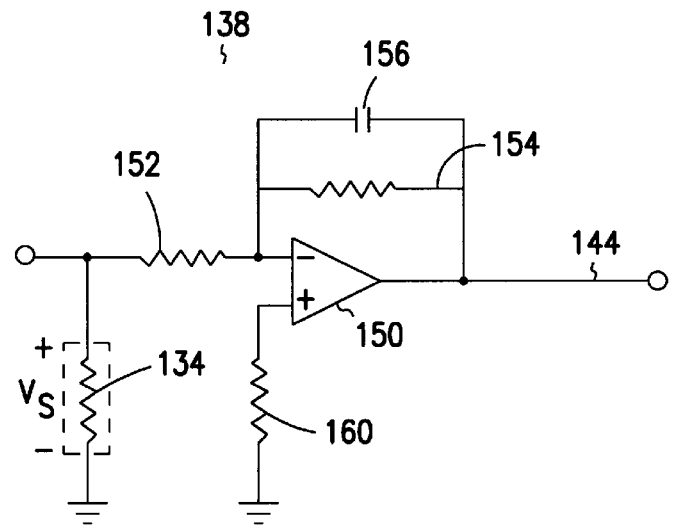
FIG. 11 is a detailed schematic of the circuitry for the alignment indicator shown in FIG. 10 in accordance with the present invention.

As noted above, the voltage waveform across the resistor 134 includes both AC and DC components. The AC component is filtered to permit examination of the DC component. Referring now to FIGS. 10 and 11, the low-pass amplifier 138 is configured as an inverting amplifier, with an operational amplifier 150, an input resistor 152, a feedback resistor 154, a feedback capacitor 156, and an output resistor 158. The negative ratio of the resistance of feedback resistor 154 to the resistance of the resistor 152 determines the DC voltage gain of the amplifier 138. Preferably, the gain is set at 100. Therefore, the resistance of resistor 154 should be one hundred times greater than that of resistor 152. Resistance values of 44.9 Kohms for resistor 154 and 449 ohms for resistor 152 are exemplary, but numerous other values are possible. The capacitor 156, together with resistor 152, provide low-pass filter capabilities to amplifier 138. A resistor 160 connects the non-inverting input terminal of operational amplifier 150 to ground. The output terminal of operational amplifier 150 connects to feedback resistor 154, the capacitor 156, and output resistor 158. The output of amplifier 138 (which preferably indicates a negative voltage value) is provided on conductor 144 to the peak detector 140.

Figure 12:
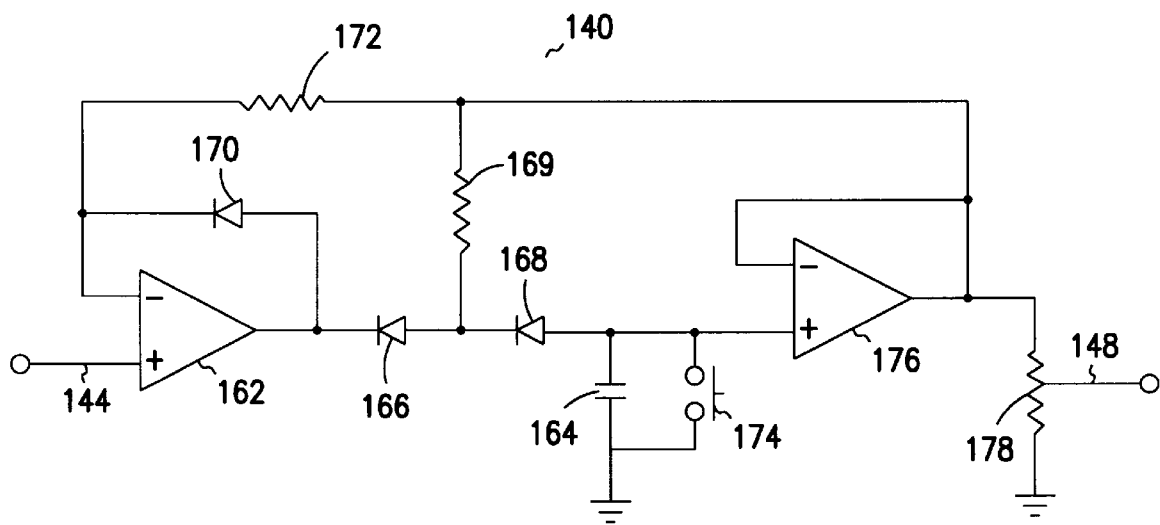
FIG. 12 is a detailed schematic of the circuitry for the peak detector shown in FIG. 10 in accordance with the present invention.

Referring now to FIGS. 10 and 12, the detailed construction and operation of the peak detector 140 will now be described. The peak detector 140 includes an operational amplifier 162, a peak storage capacitor 164, and voltage follower 176. The low-pass amplifier 138 connects through the conductor 108 to the noninverting input terminal of the operational amplifier 162. The output terminal of operational amplifier 162 connects to the cathode of diode 166, the anode of which connects to the cathode of diode 168. Current from the operational amplifier 162 (with a negative amplitude) flows through the diodes 166 and 168, charging storage capacitor 164 to a voltage indicative of the peak value at the non-inverting input of operational amplifier 162. A diode 170 prevents operational amplifier 162 from saturating in the absence of peak values, and a resistor 172 provides a path through which the current from the diode 170 can flow. A switch 174 resets the peak detector output signal to 0 V upon closure of that switch 174.

When a new peak arrives at the non-inverting input of operational amplifier 162, the output of operational amplifier 162 swings in the negative direction, turning the diode 170 off and turning the diodes 166 and 168 on, permitting the capacitor 164 to charge. As the input voltage on the conductor 144 drops, the output of the operational amplifier 162 swings in the positive direction, turning off the diode 166 and diode 168. As a result, the capacitor 164 maintains its peak voltage charge, with the diode 168 and resistor 169 limiting the leakage of the capacitor 164. As the output voltage continues in the positive direction, the diode 170 turns on to prevent saturation of the operational amplifier 162.

The voltage follower buffer 176 is provided to not only provide a high input impedance to minimize loading on other stages of the circuitry, but also to scale down the peak detected voltage through the use of a manually adjustable potentiometer 178. The potentiometer 178 connects between the output of the voltage follower 176 and ground to provide an adjustable voltage divider in which a conductor 148 carries the scaled down peak voltage to an input of differential amplifier 142. The output of the voltage follower 176 is fed back to the inverting input of the follower 176.

Figure 13:
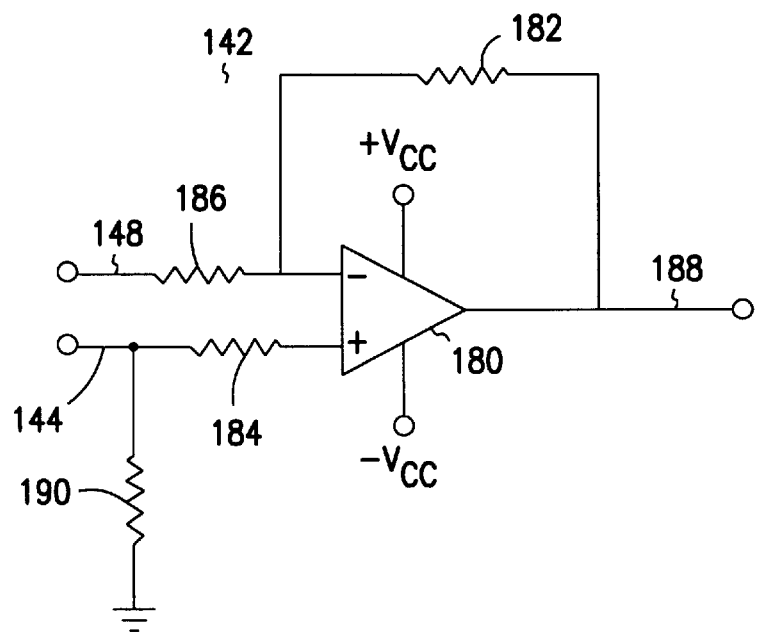
FIG. 13 is a detailed schematic of the circuitry for the amplifier in the alignment indicator shown in FIG. 10 in accordance with the present invention.

Referring now to FIG. 13, the differential amplifier 142 includes an operational amplifier 180, a feedback resistor 182, and input resistors 184, 186. The output signal from the peak detector 140 couples to the inverting input terminal of operational amplifier 180 through the resistor 186. The output signal from the low-pass amplifier 138 couples through the resistor 184 to the noninverting input terminal of operational amplifier 180. The operational amplifier 180 amplifies the difference between the scaled peak value on the conductor 148, and the present sensed value on the conductor 144, and provides the amplified difference as its output 188. In the embodiment of FIG. 13, the resistance of the resistor 182 is equal to the resistance of the resistor 190, and the resistance of resistor 186 is equal to the resistance of resistor 184, to provide a gain for difference amplifier 142 that equals the ratio of resistor 182 to resistor 186.

Figure 14:
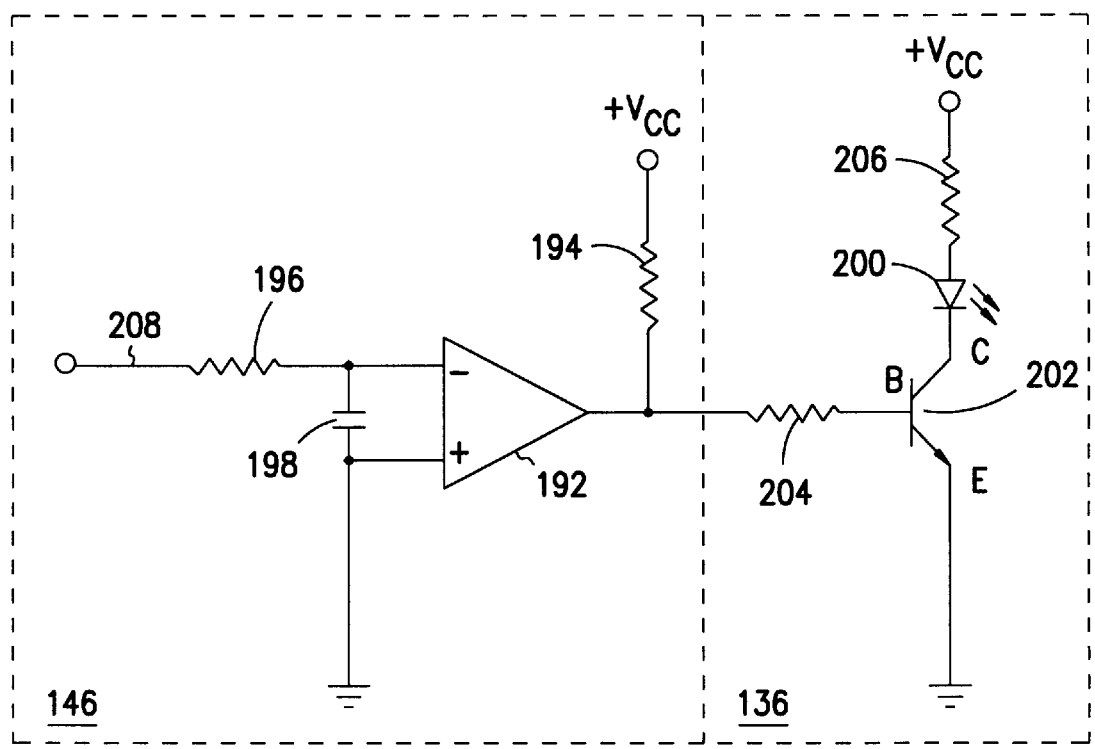
FIG. 14 is a detailed schematic of the circuitry for the comparator and the LED circuit in the alignment indicator shown in FIG. 10 in accordance with the present invention.

Referring now to FIGS. 10 and 14, the comparator 146 and the LED circuit 136 are shown in detail. The comparator circuit 146 includes a comparator 192, a pull-up resistor 194; an input resistor 196, and a capacitor 198. The LED circuit 136 includes an LED 200, a transistor 202, and current limiting resistors 204 and 206. The output of the differential amplifier 142 connects via a conductor 208 to the inverting terminal of the comparator 192, through the input resistor 196. The non-inverting input terminal of comparator 192 connects to ground, and to the inverting input terminal of the comparator 192 through the capacitor 198. The output of the comparator 192 provides an input signal to the LED circuit 136 to turn on the LED 200, or an alternative output device. The resistor 194 is a pull-up resistor which may be necessary if the comparator 192 has an open-collector output stage. In the illustrated embodiment, the output terminal of the comparator 192 connects to the gate of the transistor 202 through the current limiting resistor 204. Power from the voltage source $+V_{cc}$ is provided to the LED 200 through the resistor 206 when the transistor 202 is turned on by the supply of sufficient current from the comparator 192 to the gate of the transistor 202. Although an NPN transistor is shown in FIG. 14, one of ordinary skill in the art will recognize that other types of LED driver circuits are possible, including the use of PNP transistors, among others. Similarly, although an LED 200 is shown as the output device, it will also be understood that other output devices, such as audible indications, may be used as an alternative, or in addition to the LED 200.

One of ordinary skill in the art will recognize that a plurality of circuit implementations are possible for the low-pass amplifier 138, the peak detector 140, the differential amplifier 142, the comparator 146, and the LED circuit 136 of the alignment indicator 82. In addition, the functions of two or more of these components may be performed by a single device.

Figure 15:
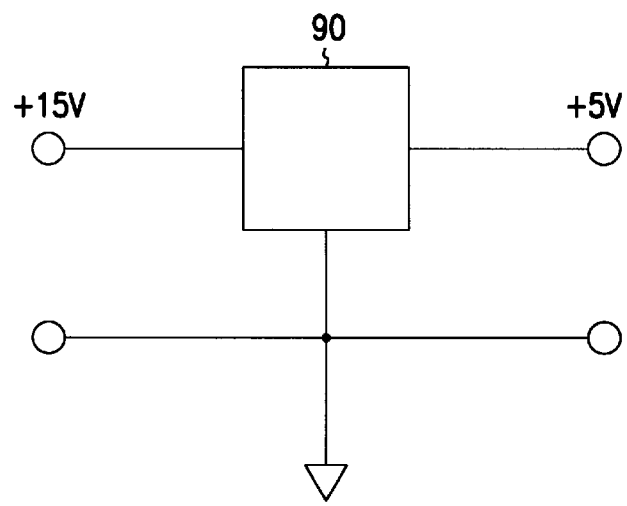
FIG. 15 is a detailed schematic of the circuitry for the regulator shown in FIG. 9 in accordance with the present invention.
Figure 16:
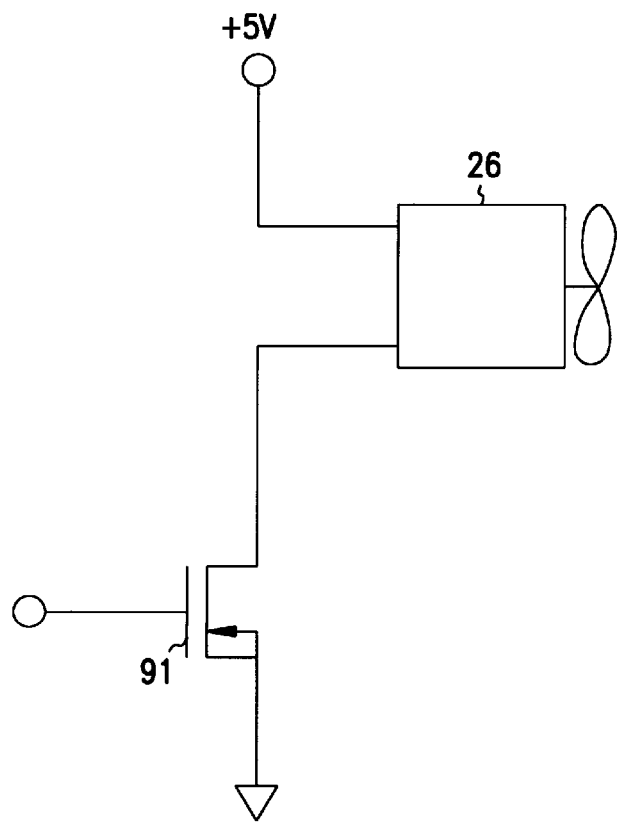
FIG. 16 is a detailed schematic of the circuitry for the switch in FIG. 9 in accordance with the present invention.

The fan 26 may be configured to run continuously as long as power is supplied to the AC/DC converter 28. Alternatively, the TET system 10 may be provided with circuitry to regulate the operation of the fan 26 in relation to the temperature of the implantable device 25. The structure and operation of the regulator 90, the comparator 86, the switch 91, and the telemetry receiver 84 may be understood by referring to FIGS. 9, 15 and 16. The regulator 90 receives a high voltage input (typically +15 to 40 V) from the AC/DC converter 28 and reduces the voltage to a level that is suitable for the particular size of fan 26 selected. In the illustrated embodiment, the voltage is stepped down to approximately +5V. The +5V output is connected to one terminal of the fan 26. The regulator 90 may be implemented in a variety of circuits. In the illustrated embodiment, the regulator 90 is an integrated circuit, model LM78M05 supplied by Motorola.

The other terminal of the fan 26 is connected to the switch 91. The switch 91 is shown implemented as a MOSFET device, though other types of switches may be used as well. The drain of the switch 91 is tied to ground and the gate is tied to the output of the comparator 86. The switch 91 is closed and current is allowed to flow from the regulator 90 into the fan 26 depending on the output of the comparator 86.

The comparator 86 compares signals from the receiver 84 to a reference voltage $V_{ref}$ and supplies an output that controls the switch 91. In this regard, one input of the comparator 86 is connected to the reference voltage source 88 and the other input is connected to the output of the receiver 84. The reference voltage source is designed to supply a reference voltage that represents the maximum allowable temperature of the can 41 at which the fan 26 is turned on and off. The comparator 86 may be implemented in a variety of well known circuits. It is anticipated that the comparator 86 should be designed with a hysteresis equivalent to at least 0.5° C. so that noise in the system will not affect the cycling on and off of the fan 26, and so that the temperature in the tissue surrounding the can 41 will be maintained below the acceptable maximum temperature without excessively frequent cycling of the fan 26 on and off.

The receiver 84 receives telemetry signals from the telemetry transmitter 100 in the implantable device 25. The transmitter 100 encodes and transmits temperature signals generated by the temperature sensor 98 in the implantable device 25. The temperature sensor 98 may be designed to sense the temperature of the can 41 or the components inside the can 41. The transmitter 100 and the receiver 84 may be any conventional telemetry system commonly found in many implantable devices. Alternatively, the dedicated transmitter 100 and receiver 84 may be replaced by using the secondary coil 92 as a telemetry transmitter and the induction coil 24 as a telemetry receiver.

The comparator continuously compares the temperature voltage signal from the receiver 84 with the reference voltage $V_{ref}$. For the purpose of this illustration, assume that the output of the comparator is low as long as the voltage signal from the receiver 84 is less than $V_{ref}$. In this state, the gate of the switch 91 is low and the fan 26 is off. This represents the condition when the temperature of the can 41 is below the accepted maximum temperature for the surrounding tissue. If the temperature of the can 41 exceeds the preselected maximum value, the output of the comparator will swing high closing the switch and turning on the fan 26. The fan 26 will continue to run until the temperature of the can 41 falls below the accepted maximum. In practice, the temperature at which the fan 26 will switch on should be slightly lower than the true maximum acceptable temperature for the surrounding tissue to account for the time lag that will exist between the instant the temperature rise in the can 41 is sensed and the time when the convective heat transfer produced by the fan 26 can begin to lower the temperature of the skin 34.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A transcutaneous energy transfer system for transferring energy to an implantable medical device, comprising:

a housing having a lower surface and a base for supporting the housing above a patient's skin and thereby defining a space between the lower surface and the patient's skin;

an induction coil disposed in the housing for transferring energy to the implantable medical device; and an electric fan coupled to the housing for moving air through the space.

2. The transcutaneous energy transfer system of claim 1, comprising a regulator for controlling the operation of the electric fan in response to the temperature of the implantable device.

3. The transcutaneous energy transfer system of claim 2, wherein the regulator has a receiver for receiving telemetry temperature signals from the implantable medical device, a reference voltage source, and a comparator for comparing the telemetry temperature signals received by the receiver with the reference voltage, whereby the regulator can turn the electrical fan on and off depending upon the output of the comparator.

4. The transcutaneous energy transfer system of claim 2, wherein the regulator has a reference voltage source and a comparator, the induction coil being operable to receive telemetry temperature signals from the implantable medical device and the comparator being operable to compare the telemetry temperature signals received by the induction coil receiver with the reference voltage, whereby the regulator can turn the electrical fan on and off depending upon the output of the comparator.

5. The transcutaneous energy transfer system of claim 1, comprising an alignment indicator for indicating the degree of alignment between the induction coil and the implantable medical device.

6. The transcutaneous energy transfer system of claim 5, comprising a duct coupled to the housing and to the fan coupled to the housing for providing an enclosed airway between the fan and the space.

7. The transcutaneous energy transfer system of claim 1, wherein the base comprises at least two peripherally spaced legs.

8. A transcutaneous energy transfer system for transferring energy to an implantable medical device, comprising:

a housing having a lower surface and a base for supporting the housing above a patient's skin and thereby defining a space between the lower surface and the patient's skin;

an induction coil disposed in the housing for transferring energy to the implantable medical device;

a controller coupled to the induction coil for controlling power supplied to the induction coil;

an electric fan coupled to the housing for moving air through the space; and a regulator for controlling the operation of the electric fan in response to the temperature of the implantable device.

9. The transcutaneous energy transfer system of claim 8, wherein the regulator includes a receiver for receiving telemetry temperature signals from the implantable medical device, a reference voltage source, and a comparator for comparing the telemetry temperature signals received by the receiver with the reference voltage, whereby the regulator can turn the electrical fan on and off depending upon the output of the comparator.

10. The transcutaneous energy transfer system of claim 8, wherein the regulator has a reference voltage source and a comparator, the induction coil being operable to receive telemetry temperature signals from the implantable medical device and the comparator being operable to compare the telemetry temperature signals received by the induction coil receiver with the reference voltage, whereby the regulator can turn the electrical fan on and off depending upon the output of the comparator.

11. The transcutaneous energy transfer system of claim 8, comprising an alignment indicator for indicating the degree of alignment between the induction coil and the implantable medical device.

12. The transcutaneous energy transfer system of claim 8, wherein the base comprises at least two peripherally spaced legs.

13. The transcutaneous energy transfer system of claim 8, comprising a duct coupled to the housing and to the fan for providing an enclosed airway between the fan and the space.

14. A recharger for transcutaneously recharging a battery in an implantable medical device, comprising:

a housing having an annular chamber, an upper surface, a lower surface, a passage extending from the upper surface to the lower surface and being substantially concentric with the annular chamber, and a base for supporting the housing above a patient's skin and thereby defining a space between the lower surface and the patient's skin;

an induction coil encased within the annular chamber for transferring energy to the battery;

an electric fan coupled to the housing and being disposed within the passage for moving air through the space;

a controller coupled to the induction coil for controlling power supplied to the induction coil; and a regulator for controlling the operation of the electric fan in response to the temperature of the implantable device.

15. The recharger of claim 14, wherein the regulator includes a receiver for receiving telemetry temperature signals from the implantable medical device, a reference voltage source, and a comparator for comparing the telemetry temperature signals received by the receiver with the reference voltage, whereby the regulator can turn the electrical fan on and off depending upon the output of the comparator.

16. The recharger of claim 14, wherein the regulator has a reference voltage source and a comparator, the induction coil being operable to receive telemetry temperature signals from the implantable medical device and the comparator being operable to compare the telemetry temperature signals received by the induction coil receiver with the reference voltage, whereby the regulator can turn the electrical fan on and off depending upon the output of the comparator.

17. The recharger of claim 14, comprising an alignment indicator for indicating the degree of alignment between the induction coil and the implantable medical device.

18. The recharger of claim 14, wherein the base comprises at least two peripherally spaced legs.

* * * * *